(12) United States Patent
Kolbel

(10) Patent No.: US 6,435,179 B1
(45) Date of Patent: Aug. 20, 2002

(54) INHALATION DEVICE

(76) Inventor: Gert F. Kolbel, Wietze-Aue 34 D-30900, Wedemark (DE)

( * ) Notice: Subject to any disclaimer, the term of this patent is extended or adjusted under 35 U.S.C. 154(b) by 0 days.

(21) Appl. No.: 09/512,904

(22) Filed: Feb. 25, 2000

(30) Foreign Application Priority Data

Dec. 24, 1999 (EP) .............................. 99125842

(51) Int. Cl.⁷ .............................................. A61M 15/00
(52) U.S. Cl. ............................ 128/204.13; 128/203.12; 128/203.23
(58) Field of Search ....................... 128/203.12, 203.22, 128/203.23, 203.25, 204.11, 204.13, 204.14, 206.29, 207.18, 200.24, 207.14

(56) References Cited

U.S. PATENT DOCUMENTS

| | | | | |
|---|---|---|---|---|
| 69,396 A | * | 10/1867 | Curtis | 128/207.18 |
| 466,130 A | * | 12/1891 | Wood | 128/207.18 |
| 867,827 A | * | 10/1907 | McCulloch | 128/207.18 |
| 1,105,934 A | * | 8/1914 | Stevens | 128/204.13 |
| 2,084,299 A | * | 6/1937 | Borden | 128/204.13 |
| 2,332,798 A | * | 10/1943 | Hunn | 128/207.18 |

* cited by examiner

Primary Examiner—Glenn K. Dawson
(74) Attorney, Agent, or Firm—Collard & Roe, P.C.

(57) ABSTRACT

A device for inhaling healing active substances and medications includes a housing containing an active substance carrier therein, this housing having at least two permanent openings for the passage of air; and one of the two permanent openings being an inhaling mouth opening and is equipped with a mouthpiece for directly holding the device with the mouth.

8 Claims, 6 Drawing Sheets

INHALATION DEVICE

BACKGROUND OF THE INVENTION

1. Field of the Invention

The present invention relates to a device for inhaling medicinal substances, or medications.

2. The Prior Art

The breathing-in or inhalation of gaseous or extremely finely atomized liquid medicinal substances or medications is a proven method for treating various illnesses or diseases of the nasopharynx and the deeper air passages. Known methods include the inhalation of hot vapors and atomized liquids enriched with medicinal substances. These substances are inhaled with the help of an electrically operated device. The goal of this procedure is to provide the finest possible dissolution of the inhaled material. This is because if the material is dissolved with a very fine degree of dissolution, the active ingredients contained in the suspended droplets can penetrate deeper into the air passages and up to the smallest bronchial branches.

The inhalation of the active ingredients contained in the droplets is uncontrolled in this procedure. Thus the flow of breathing air necessarily only picks up the amount of active ingredients that is carried along at the given time by an atomizer, or which is contained in the hot vapor. It is not known to admit the active ingredients into the flow of breathing air during the inhalation in a controlled or metered or dosed manner.

It is possible to have an inhalation apparatus, including a table top device, which has a rather large structural size. The mouthpiece or breathing mask must be pressed against the user's mouth by hand. In connection with table top devices, it is also necessary to sit with the upper part of the user's body bent forward and to place the user's face against the inhalation mask.

The inhaling person is required to maintain such a position for the duration of the inhalation process and is prevented from pursuing other activities during this time. Due to the handling of the device, which is cumbersome to some extent, it is not possible to carry out continuous inhalations over a span of several hours or even over night. However, it may be desirable to carry out such continuous inhalations over a several hour time period if required by the nature of the illness.

SUMMARY OF THE INVENTION

It is an object of the present invention to provide a device for inhalation purposes which is not tied to a location and which can be used by the patient for several hours. This use can be done without requiring the patient to interrupt for this purpose any other activity or work.

The above object is achieved by the present invention which provides an active substance carrier being arranged in a housing having two permanent openings, whereby one of said openings is provided as an inlet opening for admitting aspirated fresh air, and the second opening serves as an inhalation opening and is equipped with a mouthpiece for directly holding the device with the mouth.

The small device according to the invention avoids the disadvantages created by the known designs of such prior art devices. Thus it can be manufactured in a substantially simpler way and also offered at a more favorable price. The dosing of the inhaled substance can be controlled, for example by a cover partly covering the active substance carrier. The active substances are solely transported by the breathing air, to which the active ingredients are admixed by evaporation. It is possible in this way to provide the active ingredient with a substantially finer distribution in the breathing air. Thus the active ingredient can penetrate without problems into the smallest branches of the bronchi. The effect of the medication so administered is enhanced at the same time.

No operation of the device by external energy is required, and the device is not tied to the availability of an electric current source. The higher temperature of the exhaled flow of air preheats ethereal oils for the subsequent inhalation and assures that active substances are made available in a superior way. Excessive tempering (or overheating) is avoided at the same time. Not every active substance is capable of providing or maintaining its healing property at temperatures far above the body temperature.

The inhalation device according to the invention is equipped with a mouthpiece, which is held between the front row of teeth and the lips in front of this row of teeth. A good fit or positioning of the device is assured even when the lip muscles are relaxed, for example while sleeping. The breathing air is not subjected to any unnecessary resistance as it exclusively flows through the device according to the invention. The cross sections of the openings through which the breathing air is flowing can be selected in such a way that an unlimited supply of oxygen can be offered even if breathing air is needed in increased amounts, for example during light physical exercising.

According to a further embodiment of the device of the invention, provision can be made for two additional openings for plugging on nose tubes. These nose tubes guide the flow of breathing air not only through the cavity of the mouth, but also through the nasal region.

Both hands remain free during inhalation, and the patient is not tied up, but is able to do his or her professional work while inhaling. Furthermore, the patient can ride on his or her bicycle or by car; or the patient can sleep or can even speak.

In addition to being employed for healing treatments, the inhalation device according to the invention can be used in another area of application. This other application includes an environment of bacterially polluted air or unhealthy air. It is possible to supply the user with healthier air, for example germ-free breathing air, by using in the device certain ethereal oils or other active substances.

With a cover sleeve which is open on one side, the carrier of the active substance can be completely closed. When the device is used, the active substance can be continuously exposed until the breathing air is completely released. A particularly simple yet effective dosing of the active substance into the flow of the breathing air can be achieved in this way. If the carrier of the active substance is completely closed, the unconsumed amount of active substance is stored and can be carried along for later use.

Through continuous inhalation also during nights, it is possible in particular for seriously ill patients, for example asthmatics, to suppress onsets of an attack continuously, and not only for short time intervals.

BRIEF DESCRIPTION OF THE DRAWINGS

Other objects and features of the present invention will become apparent from the following detailed description considered in connection with the accompanying drawings which disclose several embodiments of the present invention. It should be understood, however, that the drawings are designed for the purpose of illustration only and not as a definition of the limits of the invention.

In the drawings, wherein similar reference characters denote similar elements throughout the several views.

DETAILED DESCRIPTION OF PREFERRED EMBODIMENTS

Figure 1:
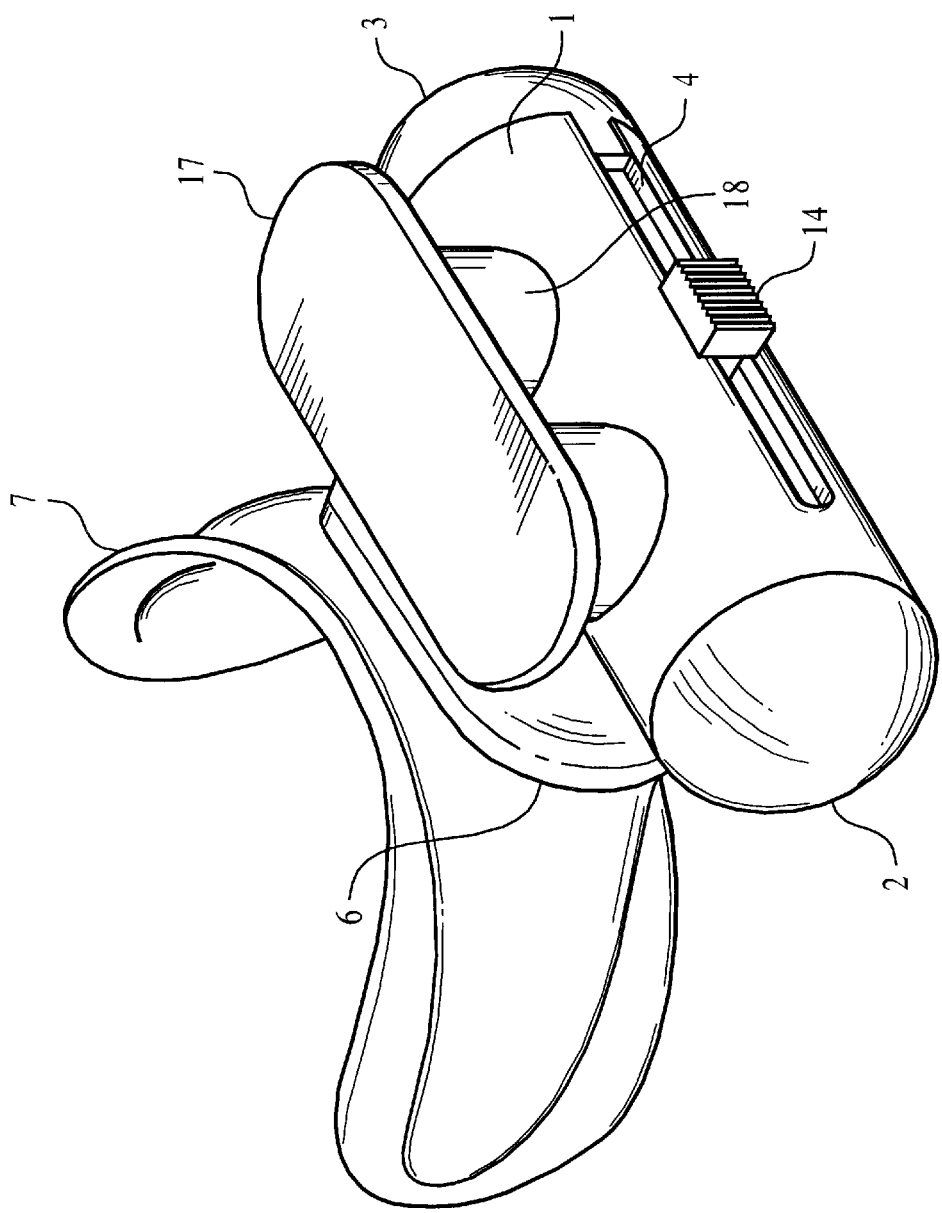
FIG. 1 is a perspective view of the invention device with closed nose openings.
Figure 2:
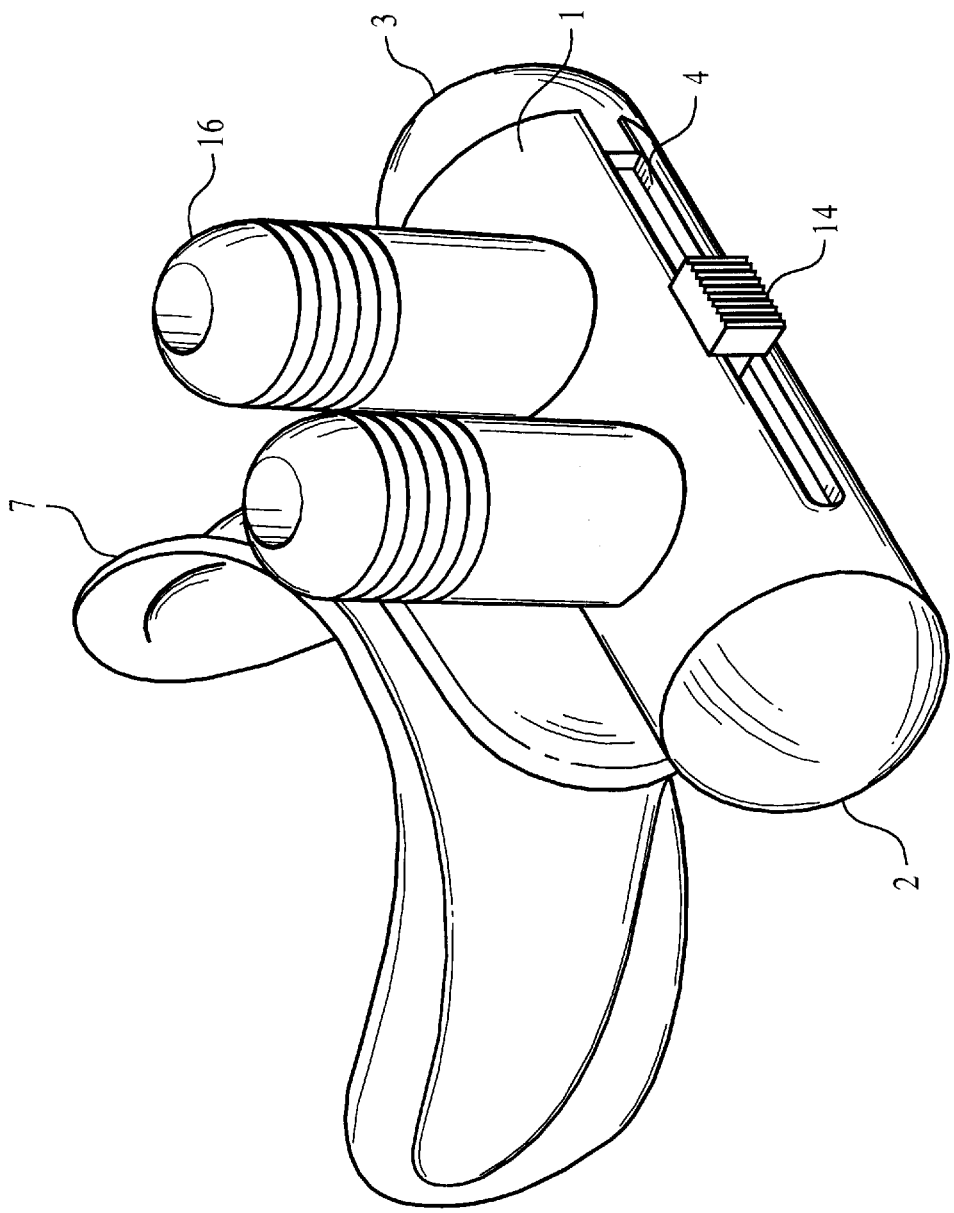
FIG. 2 shows a perspective view of the invention device with plugged-on nose tubes for inhalation through the nostrils.
Figure 3:
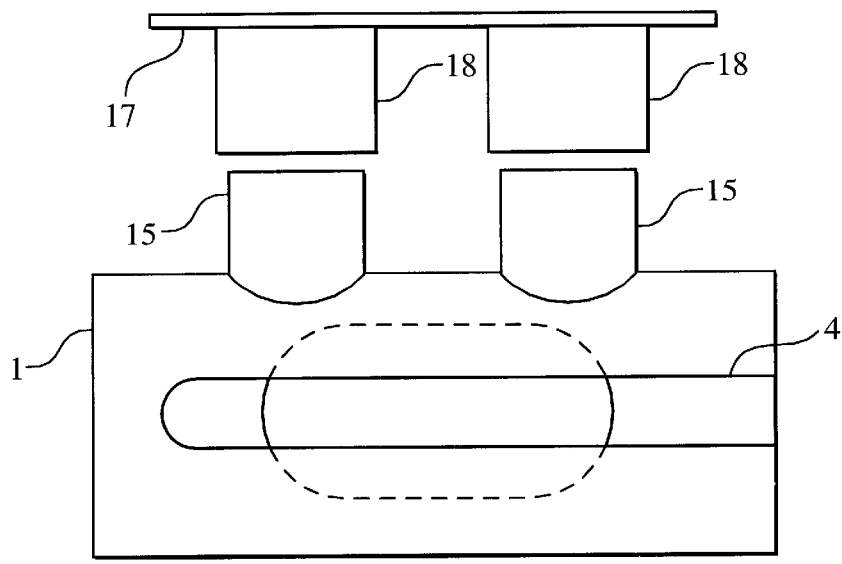
FIG. 3 is a side view of the sleeve-like center part of FIG. 2.
Figure 4:
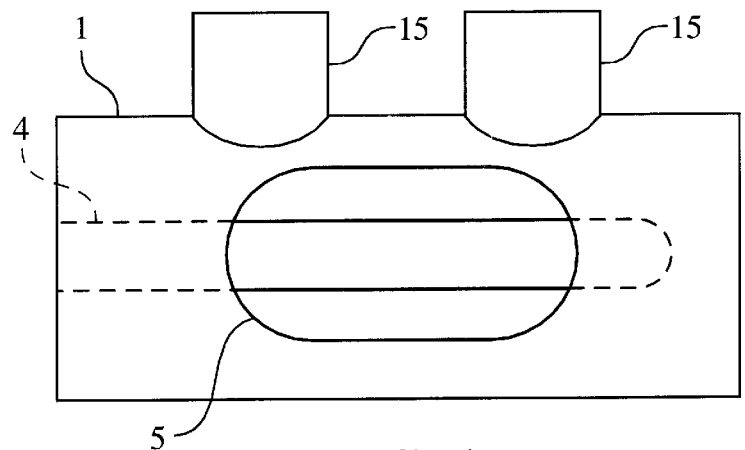
FIG. 4 shows the center part from the back, with the connection opening for connecting the mouthpiece.
Figure 5:
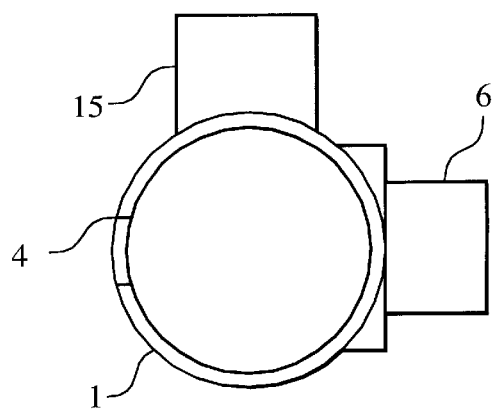
FIG. 5 is a side view of the center part.

Turning now in detail to the drawings, FIGS. 1 and 2 show the inhalation device having a cylindrical center part 1 with the semispherical end caps 2 and 3. The center part has a slot-like opening 4 as shown in FIG. 3 for letting in fresh air admitted into the interior. There is an opening on the mouth side for letting out fresh air enriched with active substances, and letting in the return flow of exhaled air. The mouthpiece 5 as shown in FIG. 4 is fitted with a connection socket 6 as shown in FIG. 5 for sliding on a mouthpiece 7 made of highly elastic material.

Figure 6:
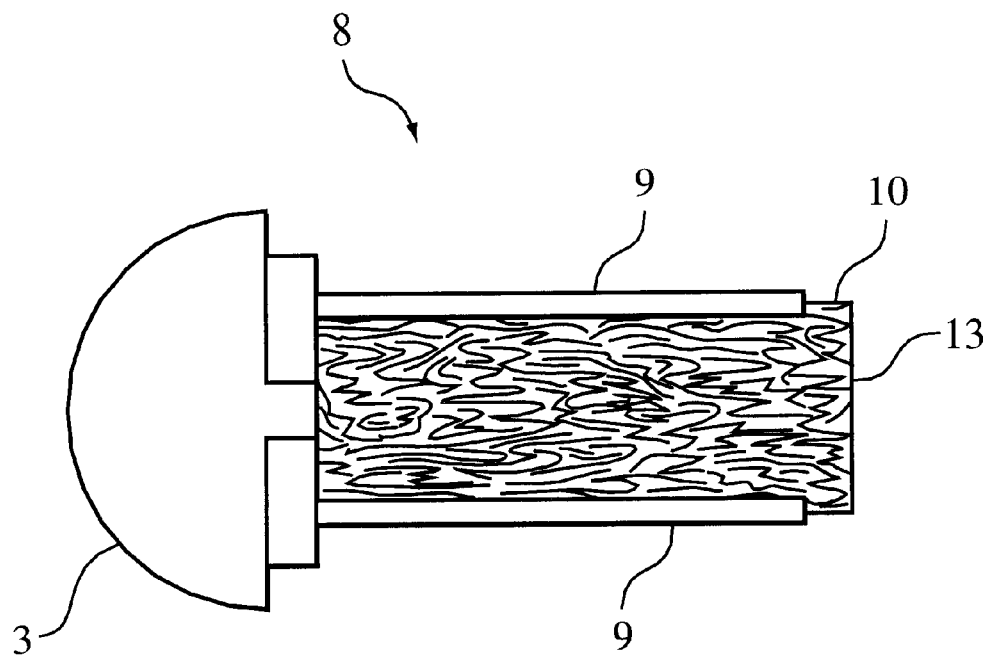
FIG. 6 is a side view of the active substance holder.
Figure 7:
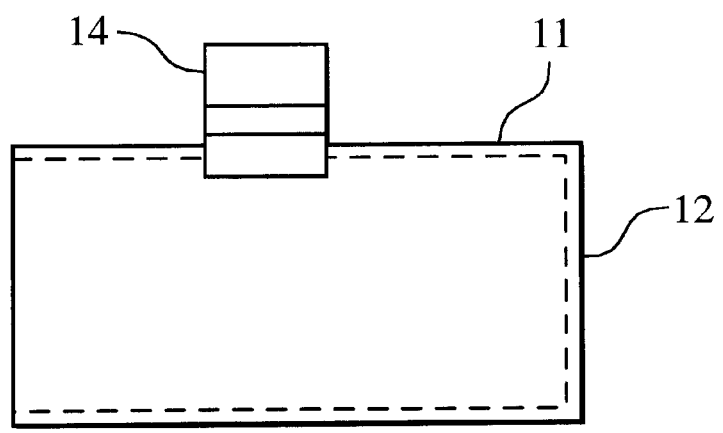
FIG. 7 shows the dosing sleeve.

An active substance carrier 8 as shown in FIG. 6 is arranged in the interior of the center part 1. This carrier 8 is made of several elastic arms 9, and preferably four elastic arms which are directly connected with the end cap 3. These arms hold a wick or porous tampon 10, which is enriched or saturated with ethereal oils or other active substances, and held by slight clamping. A sleeve-like dosing cap 11 as shown in FIG. 7 can be pushed over the active substance carrier. The bottom 12 of the dosing cap 11 can be pushed up to and against the face side end 13 of the wick 10, hermetically sealing the active substance carrier, so that no further active substance can evaporate. With a hand button 14, the dosing sleeve 11 can be displaced in the longitudinal direction of the center part 1. The button 14 is guided in the slot-like opening 4.

In addition, provision is made for two openings for inhaling through the nose. These two openings are provided with the cylindrical connections 15 as shown in FIG. 3 for plugging on the nose tubes 16 as shown in FIG. 2.

Figure 8:
FIG. 8 shows the invention device being used for inhaling through the mouth.
Figure 9:
FIG. 9 shows the invention device for inhaling both through the mouth and the nose.

If a patient wishes to inhale only through the mouth (see FIG. 8), the nose openings can be closed with the help of a cover plate 17, as shown in FIG. 3, which has two closing caps 18 located on its underside. During inhalation, therefore, breathing air enriched with active substances can be inhaled both through the mouth opening 5 and the nose tubes 16 (see FIG. 9). The active substance carrier cantilevering from a face side of the center part into the interior is then released more or less by sliding or displacing the dosing sleeve 11 sideways. This will permit the active substance in this way to evaporate in metered amounts into the breathing air.

Accordingly, while a few embodiments of the present invention have been shown and described, it is to be understood that many changes and modifications may be made hereunto without departing from the spirit and scope of the invention as defined in the appended claims.

What is claimed is:

1. A device for inhaling healing active substances and medications comprising a housing (1, 2, 3) containing an active substance carrier (8) therein, said housing having at least two permanent openings (4, 5) for the passage of air;

one of said two permanent openings being an inhaling mouth opening (5) and is equipped with a mouthpiece (6, 7) for directly holding the device with the mouth;

wherein the active substance carrier (8) comprises four elastic arms (9), and said four elastic arms holding a wick or tampon under slight pretension; and said wick or tampon being impregnated with said healing active substance.

2. The device according to claim 1, comprising a face-side closing cap (3) for attaching the elastic arms (9) which are directly secured thereon.

3. The device according to claim 1, comprising a dosing sleeve (11) sliding over said carrier (8) for covering the active substance carrier.

4. The device according to claim 1, wherein the housing has two additional nose inhalation openings connections (15) provide with plug-on nose tubes (16).

5. The device according to claim 4, wherein the nose inhalation openings can be closed with the help of closing caps (18) when not in use.

6. The device according to claim 5, wherein the closing caps are connected with each other by a connecting plate-like bridge (17).

7. The device according to claim 1, wherein the mouthpiece (6, 7) is made of a highly elastic plastic adaptable to any shape of the maxilla.

8. A device for inhaling healing active substances and medications comprising housing (1, 2, 3) containing an active substance carrier (8) therein, said housing having at least two permanent openings (4, 5) for the passage of air;

one of said two permanent openings being an inhaling mouth opening (5) and is equipped with a mouthpiece (6,7) for directly holding the device with the mouth; and a suction opening for aspirating fresh air (4) which is slot-shaped and guides an actuating button (14) of a dosing sleeve (11).

* * * * *